United States Patent
Weissgerber et al.

(10) Patent No.: US 6,712,085 B2
(45) Date of Patent: Mar. 30, 2004

(54) METHOD FOR THE PROVISION OF FLUID VOLUME STREAMS

(75) Inventors: Hans-Georg Weissgerber, Straubenhardt (DE); Bernd Glatz, Friolzheim (DE)

(73) Assignee: Agilent Technologies, Inc., Palo Alto, CA (US)

( * ) Notice: Subject to any disclaimer, the term of this patent is extended or adjusted under 35 U.S.C. 154(b) by 25 days.

(21) Appl. No.: 10/213,666

(22) Filed: Aug. 8, 2002

(65) Prior Publication Data

US 2003/0116195 A1 Jun. 26, 2003

(30) Foreign Application Priority Data

Dec. 21, 2001 (EP) .............................. 01130574

(51) Int. Cl.⁷ ............................ G05D 7/06; G01N 30/36
(52) U.S. Cl. ....................... 137/12; 137/14; 137/487.5; 137/557; 210/198.2; 210/741; 210/659; 422/70; 73/61.56
(58) Field of Search ................... 137/12, 14, 487.5, 137/557, 624.11; 210/198.2, 659, 741; 422/70; 700/282; 73/19.04, 23.22, 23.24, 23.27, 61.52, 61.56; 96/102; 95/82, 19, 22

(56) References Cited

U.S. PATENT DOCUMENTS

| | | | | |
|---|---|---|---|---|
| 4,277,832 A | * | 7/1981 | Wong ......................... | 700/282 |
| 4,373,549 A | * | 2/1983 | Nalepa et al. ............ | 137/487.5 |
| 4,882,781 A | * | 11/1989 | Allington .................... | 700/282 |
| 4,976,750 A | * | 12/1990 | Munari ......................... | 95/19 |
| 5,004,538 A | * | 4/1991 | Apfel ...................... | 210/198.2 |
| 5,040,126 A | | 8/1991 | Allington | |
| 5,071,547 A | * | 12/1991 | Cazer et al. ............. | 210/198.2 |
| 5,476,000 A | * | 12/1995 | Henderson et al. ........ | 73/23.27 |
| 6,299,767 B1 | * | 10/2001 | Dourdeville ............. | 210/198.2 |
| 6,627,075 B1 | * | 9/2003 | Weissgerber et al. .... | 210/198.2 |

FOREIGN PATENT DOCUMENTS

| | | |
|---|---|---|
| DE | 199 14 358 | 10/2000 |
| EP | 0 495 255 | 7/1992 |
| WO | WO 96/08718 | 3/1996 |

OTHER PUBLICATIONS

Muller, T. European Search Report Application No. EP 01 13 0574 dated May 29, 2002.

* cited by examiner

*Primary Examiner*—Ramesh Krishnamurthy

(57) ABSTRACT

The invention concerns a method supplying volume streams of fluids in channels or capillaries of small stream cross sections, more particularly chromatographic separating columns for the analytical fluid metrology, wherein a delivery device for delivering a volume stream of the fluid through an operating channel and a pressure measuring device for measuring the pressure in the operating channel is provided, wherein a measurement of the volume stream is possible, characterized by the following steps:

a) Recording a time reference pressure course using the pressure measuring device in the operating channel, while the delivery device delivers an essentially constant, pre-determinable reference volume stream through the operating channel of a fluid with properties, more particularly flow properties, varying over time;

b) Calculation of a time development of the operating pressure, which corresponds to the essentially constant and preferably small operating volume stream through the operating channel, which is different from the reference volume stream, using a pre-determinable mathematical algorithm;

c) Delivery of a fluid through the operating channel, wherein the fluid has the same flow properties over time as the fluid used in step a), using the time development of the operating pressure calculated in step b), while the desired work process, more particularly the separation or substance analysis, is performed.

12 Claims, 2 Drawing Sheets

METHOD FOR THE PROVISION OF FLUID VOLUME STREAMS

FIELD OF THE INVENTION

The invention concerns a method for the supply of fluid volume streams in channels or capillaries with small stream cross sections, more particularly in chromatographic separation columns for analytical fluid metrology, more particularly for analytical liquid chromatography, wherein a delivery device for the delivery of a volume stream of the fluid through an operating channel and a pressure measuring device for measuring the pressure in the operating channel are provided, wherein a measurement of the volume stream is possible.

DISCUSSION OF THE BACKGROUND ART

Such a method is presently used, for example, in liquid chromatography, more particularly high pressure liquid chromatography (HPLC). Depending on the inner diameter of the separating columns used, HPLC is divided into so-called "normal bore chromatography", in the case of separating columns with an inner diameter between approximately 3 and 5 mm, "micro bore chromatography", using separating columns with an inner diameter between approximately 1 and 2 mm, "capillary-LC-chromatography" using separating columns with an inner diameter between approximately 180 and 320 μm, and "nano-LC chromatography", using separating columns with an inner diameter equal to or smaller than 100 μm.

The supplied flow rates must be adapted to the inner diameter of the column according to the application. While flow rates in the range of ml/min and μm/min are common in normal bore technology and micro bore technology, flow rates in the range of as low as several 100 nl/min must be realized in nano-LC technology. The flow rates are commonly adjusted so that in the separating column a linear stream velocity of approximately 1 to 2 mm/s is achieved. This is important because the efficiency of a separating column depends on the flow rate.

The application of separating columns with an inner diameter of less than 180 μm is gaining interest not only in high pressure liquid chromatography but also in the area of other microfluid systems. While in high pressure liquid chromatography the volume stream is commonly generated using a hydraulic pump, electric osmosis is often used to create the volume streams in microfluid systems. Evidently, it is also possible to combine hydraulically pumps with microfluid systems. A particular example of such a microfluid system is a microfluid chip.

Another important point in the connection with an optimum flow rate is the detection of the substances to be analyzed. Mass-selective detectors are increasingly being used. The use of such detectors requires suitable preparation and supply of the substances to be analyzed. For this purpose, the operating stream can be atomized, ionized and partially or completely dried after passing through the separating column. The individual ions stream into the opening of the detector while the solvent excess that might still exist is waste. Various methods are known for the creation of the ions. Some methods only work in a certain range of flow rates or volume flow rates. For lower or higher flow rates, the method does not work or works with significant restrictions, i.e. the detection is less sensitive or impossible.

The lower the flow rates, the more important the effects of system volumes, in particular the dead volume or the delay volume. In the case that is of interest here, the case with extremely low flow rates, these volumes must also be flushed with a very low flow rate. Otherwise, thermodynamic effects could disturb the equilibrium of the separating column and of the detector so that undesired effects may occur. Also, high flow rates are impossible simply because of the connection capillaries with very small internal diameters and the consequent pressure drop. To ensure a high efficiency of the analysis, the volumes mentioned above should be kept as small as possible. Ideally, a flush period of one minute should be sufficient to flush the delay volume with the desired low flow rate.

In a chromatographic system, the parameter stream and pressure are always interdependent via the hydraulic resistance of the separating column and the system. However, it has become common practice to determine or define the flow. The linear stream velocity through the column must be kept constant regardless of the transported solvents and the restrictions. This does not pose a problem as long as the flow rates are high enough to either directly supply the desired flow rate or to measure the flow rate. However, if extremely low flow rates in the range of nl/min are to be supplied, the two above-mentioned methods can normally not be applied.

For the above-mentioned applications, pump systems are required that can create or transport extremely low flow rates or volume streams. The delivery must be highly reliable at the high existing pressures in the range of approx. 400 bar.

For the delivery and provision of such small flow rates in separating columns for liquid chromatography, in particular for "capillary LC chromatography" and for "nano-LC chromatography", the only methods currently known are as follows:

A first method is based on the application of so-called syringe pumps. Syringe pumps are special one-piston pumps. Unlike in common piston pumps, the pistons do not move back and forth during the analysis. Instead only one piston stroke is performed. This means that the syringe pumps always work in delivery mode. The pump chamber must therefore be chosen sufficiently large so that a single piston stroke is sufficient for a complete separating analysis. The pump chamber is put under pressure before the analysis by pushing the piston in the pump chamber forward. No further suction is thus performed during the separating analysis. With this method, a volume flow can be achieved that is independent of the elasticities inside the pump chamber. The elasticities of particularly the seals and the drive mechanics as well as the elasticity due to the compressibility of the solvent can be compensated for accordingly.

However, syringe pump technology has little flexibility in the realization of different analysis times and in the use of different column diameters. This is because the possible analysis time and the choice of the separating column diameter is dependent of, and limited by, the respective available maximum displacement volume of the syringe pumps. In addition, only one high pressure gradient can be realized with a syringe pump. This means that a separate high-pressure syringe pump is necessary for every solvent used in the analysis.

Further more, the leak rate inside the delivery system plays an important role for the delivery amounts of only several nl/min. The seals and valves used for high-pressure syringe pumps typically have relatively low leak rates. Nevertheless, these leak rates can have a dramatic effect for the small flow rates used in nano-LC chromatography. Even temperature influences can cause undesired flow shifts due to thermal extension. For this reason, special thermostat arrangements and controls are often necessary.

Another possibility for the creation and provision of liquid volume streams in channels or capillaries with small diameters is the use of traditional piston pumps suitable for "normal bore chromatography". This method uses the so-called passive splitter technology, which is very common in practice. It means that suitable flow divider are used to divide the total stream created and supplied by the pump into at least two partial streams, a surplus stream in a surplus path and an operating stream in an operating path.

The regulation and provision of the respective operating stream is done by so-called restrictors, i.e. by hydraulic resistances located in the surplus path. The flow dividers, and in particular the hydraulic resistors, are usually made of so-called "fused silica capillaries" with small inner diameter. The length and the inner diameter of these elements determine the stream resistance. The total flow rate is split according to the resistance ratios. Typically, the smaller part flows through the separating column.

The advantage of this technology is the low production expenditure because the splitters and the hydraulic resistances can be produced by the users themselves. The extremely low volumes inside the flow dividers or inside the hydraulic resistances are also of advantage.

A particular disadvantage of the traditional splitter technology, however, is the fact that the users do not receive any information on the volume streams that flow through the separating column. For this reason, the volume stream must be measured at great effort, for example using miniature syringes and stop watches, to operate the separating column efficiently. Furthermore, even minute changes in the flow resistance, caused for example by dirt in the separating column frits, cause a considerable variation in the column stream. Not only the separating column, but also and in particular the restriction capillaries used for the splitter, with a diameter of 25 $\mu$m for example, have a high risk of getting plugged. Such plugs consequently cause an accordingly large retention time shift. Even more serious is the effect that the reduced column volume stream can have on the above-mentioned mass-selective detectors because, as also previously mentioned, only a small dynamic stream range is available for a sensitive detection.

In order to somewhat reduce this effect, a hydraulic pre-resistance is sometimes inserted before the splitter. This causes the effect of a plugged separating column frit on the column stream to be approximately halved while keeping the pressure drops over the separating column and the pre-resistance constant. However, the use of such pre-resistances also means that only half the pump pressure is available for the separating analysis in the separating column.

Another disadvantage of the splitter technology is that the two volumes of the operating path, including the column and the surplus path, must be adjusted to each other, which for practical reasons is not normally done. The "matching" of the volumes is therefore important so that the splitter is filled uniformly in case of time variation of the flow properties of the delivered fluid, in particular the composition or concentrations of the fluid changing over time as it is always the case during gradient operation. Otherwise, this causes an additional shift of the ratio between operating stream and surplus stream because the viscosities of the fluids in the stream branches differ. In practical applications this means that for different column dimensions, the splitters must always be adjusted as well.

From DE 199 14 358 A1, an active splitter system is known with which the operating stream can be measured and kept constant. For this purpose, a suitable sensor is located in the operating stream branch and there is variable restriction in the surplus stream branch, wherein these elements are coupled with a control device, creating a control loop.

An advantage of this technology is that any common pump for chromatography can be used and the desired controlled operating stream can be branched off. In this manner, an essentially constant operating stream can be created independently of the hydraulic resistance.

However, it is difficult to perform volumetric measurements of extremely low flow rates of only several nl/min. In addition, the sensors located in the operating stream create an additional delay volume. Additional volume, on the other hand, means longer analysis time as well as stretched or shifted gradient profiles causing lower efficiency of the separating column.

Another method is based on the delivery of liquids, using essentially constant pressure. With this method a certain pressure is determined so that when the application begins, the fluid can be delivered with the desired flow rate, i.e. the desired volume stream. The pressure is essentially kept constant over the entire analysis time.

An advantage of this method is that the pressure can be measured and controlled very well. The stream that eventually flows through the column is not taken into consideration here. The delay volume of the operating branch or path can also be kept to a minimum because it is not necessary to have a sensor element in the operating stream. The pressure is commonly measured in the total stream.

The main disadvantage of this technique is the fact that the flow rate in the operating stream must first be determined by some method. For this purpose, a micro-liter syringe is connected to the exit manually and the delivered flow rate is measured volumetrically. This procedure is very work-intensive.

Furthermore, in case of a change in the flow properties, in particular the viscosity of the fluid over time or the hydraulic resistance over time, the flow rate changes and this effect is not recognized or taken into consideration. In particular in the gradient mode, the flow rate will always change due to the time-varying viscosity of the fluid when this method is applied. Gradient operation means that a concentration profile, preferably a linear concentration profile, of solvents is purposely set and delivered over time. Usually a transition from watery solutions to organic solutions takes place.

Especially for mass-selective detectors in combination with the ionization sources used in this detectors, the constancy of the "response" of the detector depends on the current flow rate. Since the flow rate is shifted significantly during the gradient operation for methods relying entirely on pressure control, the sprayer must deliver a constant spray over a larger stream area. This requires especially large effort for so-called nano-electric sprayers for very low flow rates.

SUMMARY OF THE INVENTION

It is therefore an object of the invention to provide a method such as the above-mentioned methods with which in particular fluids with different flow properties can be delivered at essentially constant flow rates without requiring these very small flow rates to be measured directly.

This object is achieved according to a first approach of this invention according to the characteristics of claim 1 by providing the following steps:
a) Recording a time reference pressure course using the pressure measuring device in the operating channel, while the delivery device delivers preferably an essentially constant, pre-determinable reference volume stream through the operating channel of a fluid with properties, more particularly flow properties, varying over time;
b) Calculation of a time-dependent operating pressure course, which corresponds to a preferably essentially constant operating volume stream through the operating channel, wherein this stream is different from, and preferably smaller than, the reference volume stream, and wherein the operating volume stream is desired for a subsequent separating analysis or substance analysis, and wherein this calculation is performed using a pre-determinable mathematical algorithm;
c) Delivery of a fluid through the operating channel, wherein the fluid preferably has the same flow properties over time as the fluid used in step a), using the time development of the operating pressure calculated in step b), while the desired work process, more particularly the separation of substance analysis, is performed.

With these measures, even extremely low flow rates, such as the flow rates in nano-LC technology in chromatographic separating columns or in microfluid systems, more particularly microfluid chips, can be delivered reproducibly and monitored or controlled. For the delivery by the delivery device, it is irrelevant whether the operating stream is created directly or is only a partial stream of a total stream. Only one device is necessary to record the pressure that occurs for a given flow rate. Lastly, there needs to be a possibility for determining the flow rate. This can be done manually or, preferably automatically.

If the measurement of the reference volume stream is performed by one or more sensors, it is preferably irrelevant at which exact positions in the system the sensors are located. Their positions can then be freely chosen according to the needs of the user. For example, the stream monitoring can be performed at the end, i.e. after the separating column in direction of the flow. In this manner it can advantageously be avoided that the sensor creates an additional delay volume, which would cause the above-mentioned disadvantages.

The invention takes advantage of the connection between pressure and flow rate in a microfluid system, more particularly a chromatographic separating system. To perform the method according to the invention, it is useful if a control device for controlling the pressure in the operating channel and a control device for controlling the volume stream in the operating channel are used and can be operated alternatively so that in step a), the reference volume stream is kept essentially constant and so that in step c), the operating pressure is kept essentially constant.

As described above, a volume-controlled delivery is certainly desired. The most important advantages are the maximum efficiency of the microfluid system, more particularly a maximum separating rate of the column and optimized spray conditions for the entry into a mass-selective detector.

The algorithm to be applied can be determined for example by performing one or more reference measurements, using one fluid at a time, which has the same flow properties varying over time, i.e. the same time-dependent flow properties course. For these reference measurements, a different but sufficiently large reference volume stream is set each time so that it can be measured with sufficient accuracy using the available measurement methods. For the direct flow measurement, a mass flowmeter or a volumetric flowmeter is particularly suitable. Such a direct measurement of the volume stream can be performed by one or several suitable sensors. On the basis of the volume stream measurement, a suitable control device can be used to control the volume stream in a control loop such that it is essentially constant over time.

It is useful if the fluid with the time-varying flow properties is a fluid gradient. The gradient is advantageously created by mixing two liquids, preferably water and an organic solution, more particularly acetonitrile, in concentrations changing over time and by transporting the fluid mixture to the separating column. Advantageously, the concentration of water is reduced linearly while at the same time the concentration of the organic solution is increased.

It is advantageous to use the following equation as the mathematical algorithm:

$$P_A = P_R \cdot k \cdot V_A / V_R$$

where $P_A$ is the operating pressure, $P_R$ is the reference pressure, k is a variable or a factor, $V_R$ is the operating volume stream, and $V_R$ is the reference volume stream.

It is also advantageous if the factor 1 is used for k in the mathematical algorithm. This is of particular advantage for a chromatographic separating system in which, during the analysis or substance separation in the separating column, a linear flow velocity of approx 1 to 5 mm/s is desired for laminar flow.

According to an alternative approach of the invention, a method of this type with the previously described characteristics can have the following steps:
a) Recording a reference time development of the pressure, using the pressure measuring device in a operating channel, used as a reference channel, wherein this channel has a reference stream cross section, while the delivery device delivers a preferably essentially constant and pre-determinable reference volume stream through the operating channel of a fluid with properties, more particularly flow properties, varying over time;
b) Delivery of a fluid through the operating channel, wherein the fluid preferably has the same flow properties over time as the fluid used in step a), using the time development of the operating pressure that corresponds to the time reference pressure development determined in step a), wherein the operating channel has an operating cross-section that is different from the reference cross-section of the reference channel.

For this approach it is useful to choose the reference volume stream such that there is an essentially constant and linear flow velocity in the reference channel, which is useful for the execution of the second step, i.e. the actual work process of the analysis. For chromatographic separating columns, this linear flow velocity is chosen, dependent on the particle diameter of the packing material, in the range of 1 to 5 mm/s, wherein the corresponding reference volume stream can be measured experimentally or calculated with a known equation.

In the second step, the operating pressure course over time is followed as in the first step so that the same linear flow velocity as in the first step is created in the operating channel, which has a very small operating flow cross-section, such as the operating channels used in chromatographic separating columns for LC technology. This is concluded from the realization that in channels with different cross-sections the same linear flow velocity occurs when the same pressure profile is applied.

With this method according to the second approach, the same advantage can basically be achieved as in the method according to the first approach. An additional advantage of the second approach is that the intermediate step of calculating a transformed pressure course can be omitted. However, this method requires the use of two channels with different flow cross-section, more particularly two capillaries with different diameter, whereas in the first approach, the reference measurement and the work application can be performed in the same operating channel.

Both alternative procedures have the advantage that the process can be performed directly inside the operating channel so that the existing boundary conditions in the present operating system are taken into account. These boundary conditions cannot be determined with theoretical predictions or only with extremely high effort.

It is useful to use the same operating channel or separating column for the steps a) and c) of the first method according to claim 1. However, it is also possible to use a different operating channel or a different separating column for the two steps, as it is the case for the second method according to claim 4. In these cases, it is useful if, for the steps a) and c) according to claim 1 or for the steps a) and b) according to claim 4, operating channels with essentially the same hydraulic resistances are used. When using chromatographic separating columns, it is also useful if they have essentially the same length and if their packages contain particles with essentially the same particle property, more particularly particle size, particle size distribution and/or porosity. With these measures, the use of additional corrections or correction parameter can be avoided. For this purpose, it is useful if the hydraulic resistances or restrictions of the operating channels or separating columns are essentially the same for identical linear flow velocities. This avoids different gradient selectivities.

It is useful for both methods to take into account a delay volume that may exist in the operating channel, more particularly a delay volume between a mixing point where the fluid with time-varying flow properties is created and the separating column 23, in such a manner that the time of the application of the time development of the operating pressure is chosen with a certain difference delay time as correction. Consequently, a delay time correction is performed in this manner, which appears useful in case of existing delay volumes to obtain even more precise results.

It is also useful if in the application of the essentially constant reference volume stream, a reference delay time is determined for the fluid, for example by an experiment, and then the delay volume is calculated as the product of reference delay time and reference volume stream, a work delay time is calculated as the quotient of the delay volume and the chosen operating volume stream, and the difference delay volume is calculated as the absolute value of the difference between the operating delay time and the reference delay time. The operating pressure courses can then later be applied to the reference pressure courses shifted by this difference delay time. In other words, the operating pressure courses are simply shifted by the difference delay time while maintaining their relative time development. It is useful to work with relatively high delivery volume streams, which allow for a sufficiently precise measurement in the respective reference channels while, during the actual work step or work process, only extremely low volume streams are delivered through the operating channels with very small flow cross-sections. For this reason, the time of the start of the application of the respective time development of the pressure is moved back by correspondingly longer times during the work process of the separating analysis. In this manner, the time is taken into consideration that the fluid needs to overcome the delay volume when applying the time development of the operating pressure. The separating analysis can thus be performed with the extremely low flow rates or volume streams with maximum precision.

Other advantages, characteristics, and aspects of the invention can be seen from the following description section that describes two preferred embodiments of the invention using the figures.

BRIEF DESCRIPTION OF THE DRAWINGS

It is shown in.

DETAILED DESCRIPTION OF THE PREFERRED EMBODIMENT

Figure 1:
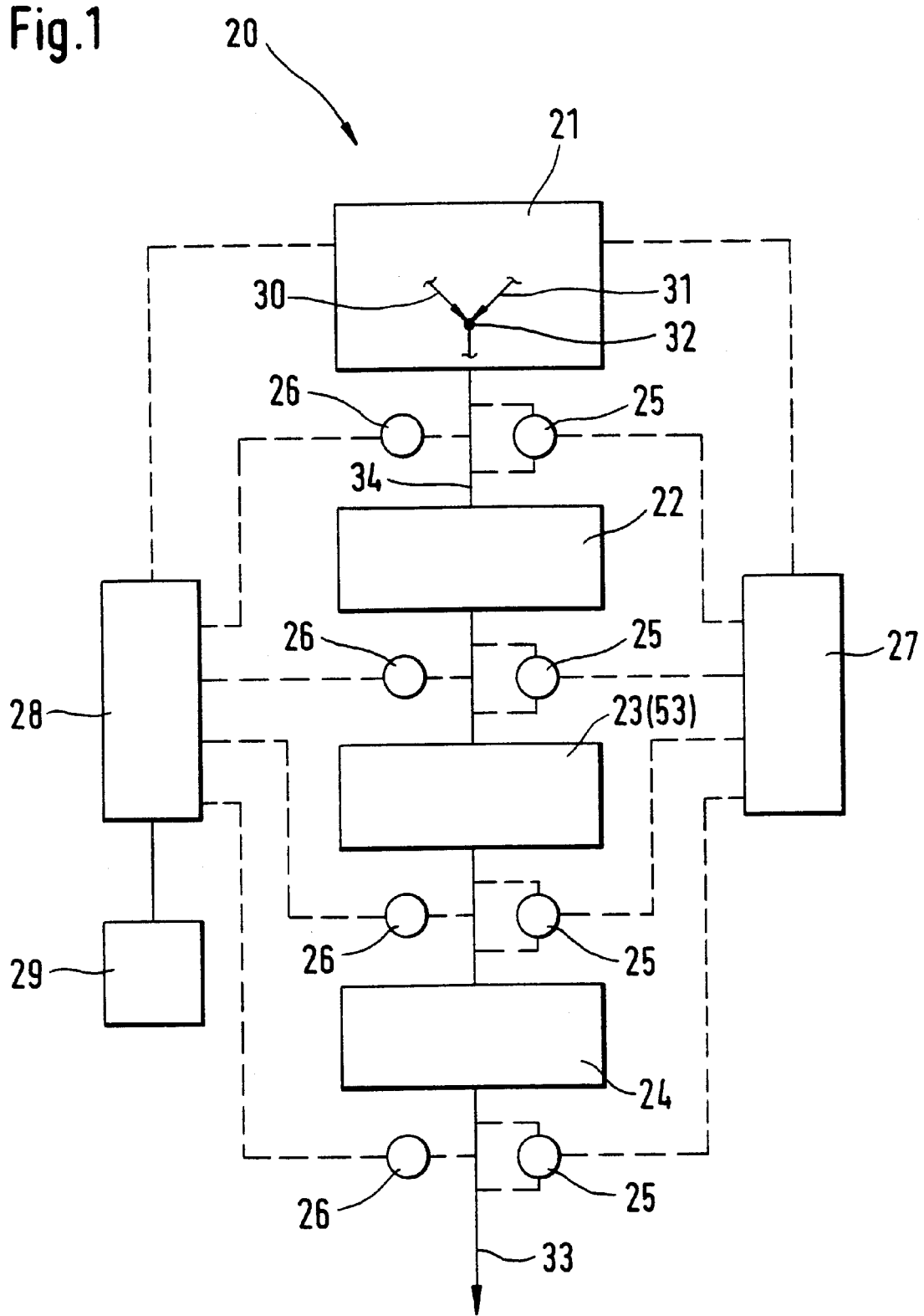
FIG. 1: A schematic side view of a device for performing the method according to this invention.

FIG. 1 shows a device 20 for performing the method according to this invention. The device in the present case is a chromatographic separating system. As essential components, it includes a pump 21, a sample receptor 22 or an injection point, a separating column 23, and a detector 24.

In order to enable gradient operation, a first path 30 and a second path 31 are provided in the area of the pump 21, wherein both parts lead to a common mixing point 32. When performing a separating analysis, the fluid 34 is delivered by the pump 21, serving as a delivery device, from the mixing point 32, through the sample receptor 22 and the separating column 23 to the detector. From there, the resulting fluid can be received by one or more container not shown in detail here.

For the recording of the volume stream of the fluid 34, one or more flow sensors 25 may be provided. The flow sensor or flow sensors 25 is or are suitable for recording or measuring relatively large volume streams with sufficient accuracy and reasonable effort. The flow sensor 25 can be located at different positions in the separating system. The dashed lines leading from the respective flow sensor 25 to the operating channel 33 indicate that the sensor 25 can be located either in the hydraulic path, i.e. the operating channel 33, or be operated in a bypass.

For the measurement of the pressure in the operating channel 33, one or more pressure sensors 26 may be provided at any suitable location. If several pressure sensors 26 are used, they may be used for the calculation of a pressure difference.

The device 20 also contains the control device 27 and the control device 28. The control device 27 is used to keep the volume streams, which are measured by the flow sensors 25 or by other means, essentially constant in order to control the volume streams through the pump 21 in a control section. The control device 27 thus allows for the operation of the pump 21 in a volume stream controlled mode. The control device 28 on the other hand is used to keep the pressures, which are measured by at least one pressure sensor to control the volume stream delivered by the pump 21, essentially constant over a second control section. The control device 28 thus allows for an alternative operation of the pump 21 in a pressure controlled mode.

A storage and computational device 29 may be connected to the control device 28 with which the measured pressures can be stored, more particularly stored in the form of time pressure profiles, and be made available in a suitable form for subsequent work processes and/or evaluation.

In the following, the method according to the invention for the supply of fluid volume streams 34 in channels or capillaries of small flow cross-sections, more particularly in chromatographic separating columns 23, for the analytical fluid metrology or the analytical liquid chromatography is described in more detail using two alternative solutions.

Both approaches have in common that a delivery device, in this case a pump 21, is used for the delivery of a volume stream of the fluid 34 through an operating channel 33 and a pressure measuring device, in this case at least one pressure sensor 26, is used to measure the pressure in the operating channel 33. Furthermore, it must somehow be possible to record the volume stream of the fluid 34 in both alternative approaches. To do so, the embodiments use at least one of the flow sensors 25.

It is advantageous if the method according to the inventions is used where a fluid is to be delivered through the operating channel and this fluid has flow properties varying over time. Flow properties may vary over time for fluids with a composition that changes over time. In particular, this case occurs regularly in the so-called gradient operation. In gradient operation, the concentration of two liquids is changed in a way, preferably in a linear manner, that the concentration of the first fluid is reduced while at the same time the concentration of the second fluid is increased. Water is used in particular for the first fluid, while the second fluid is an organic solvent, preferably acetonitrile. The first fluid is supplied to a common mixing point 32 over a first path 30 while the second fluid takes a second path 31. After this mixing point, the created fluid 34 is delivered with the aid of the pump 21, more particularly through the separating column 23.

According to the first embodiment, a reference measurement is performed in a first step. To do so, at least one of the pressure sensors 26 is used to record a reference time development of the pressure course in the operating channel 33 while the pump 21 delivers a reference volume stream of the fluid 34, essentially constant over time, in gradient operation. The reference measurement is thus performed volume stream controlled, using the control device 27. The reference volume stream in this case is chosen relatively large to allow for its sufficiently precise measurement, for example using one of the flow sensors 25. The resulting pressure development 35 over time is suitably stored, using a memory storage unit of the storage and computational device 29.

Figure 2:
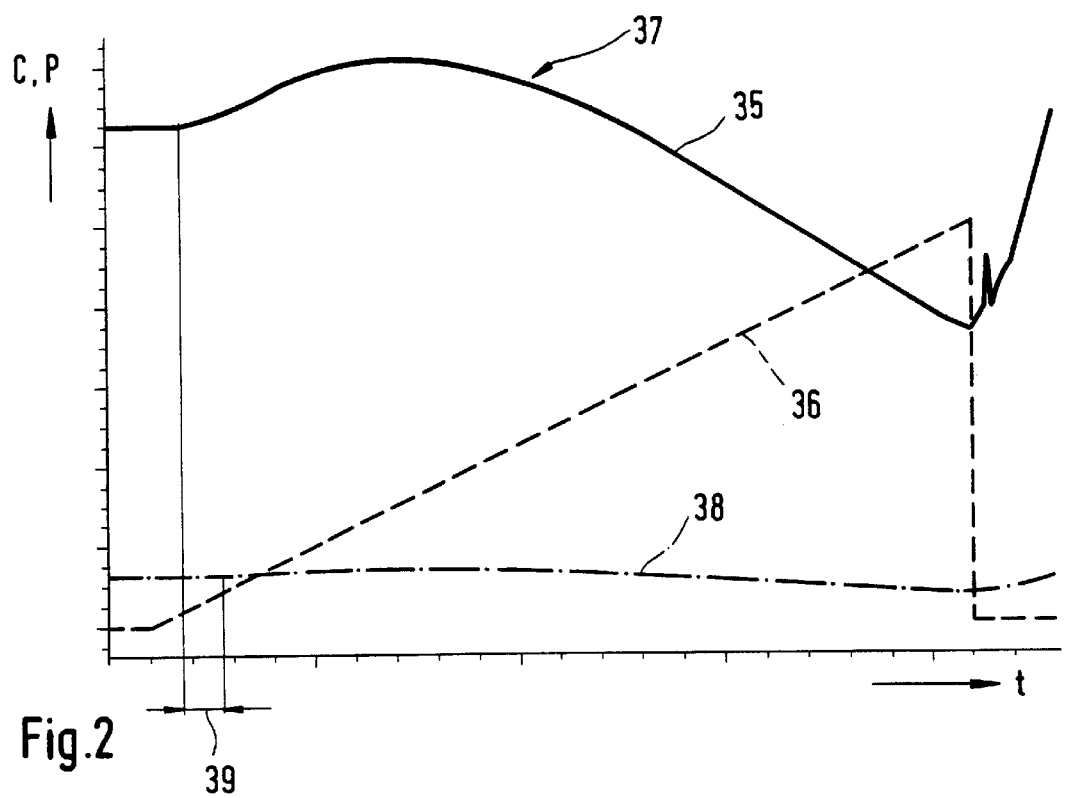
FIG. 2: a representation of two time developments of pressure profiles and a time concentration profile of a fluid that is part of a fluid mixture that has time-varying flow properties that can occur when performing the method according to a first approach.

An example for an occurring reference pressure development 35 is shown over time in FIG. 2 with the full line. The reference volume stream in this case is 590 nl/min. The time parallel concentration course 36 of acetonitrile is also shown in FIG. 2 by the dashed line, wherein the concentration is increased linearly within a certain time. The time development of the water is not shown; it is simply the opposite, i.e. the concentration is decreased parallel to time.

As it is clearly seen in FIG. 2, the volume stream controlled delivery of the fluid 34 with an essentially constant volume stream results in a non-linear reference pressure course 35. After a certain analyzing period, an increase of pressure 37 occurs respectively in the range of certain concentrations of the mixture of water and acetonitrile. This pressure rise 37 is caused by the fact that the viscosity of the fluid 34 made up of a mixture of water and acetonitrile is larger than the viscosity of pure water at a certain concentration ratio. The flow properties of the fluid 34 therefore change significantly over the time of the experiment.

After the pressure course 37 has been measured at a comparably high volume stream in the first step, the time-dependent reference pressure course 35, measured in the reference measurement and stored in the memory or storage unit according to the first embodiment, is converted into a time-dependent operating pressure course 38, using the computational unit of the computational and storage device 29 with the application of a mathematical algorithm, wherein the time-dependent operating pressure course is assigned to an essentially constant work volume stream through the operating channel 33. This work volume stream during the separating analysis is considerably smaller than during the reference measurement according to the desired flow ratios. In the example shown in FIG. 2, it is 59 nl/min.

The mathematical algorithm applied follows the equation $$P_A = P_R \cdot V_A / V_R$$

where $P_A$ is the operating pressure, $P_R$ is the reference pressure, $V_A$ is the operating volume stream, and $V_R$ is the reference volume stream. With the aid of this equation, the time reference pressure values are thus converted into the operating pressure values suitable for the separating analysis. In this manner, a corresponding operating pressure course can be calculated and stored in the memory storage unit.

Next, the separating analysis can be performed by establishing the same time development of the concentration of the liquids making up the fluid 34 in the operating channel 33 and by exactly following the operating pressure course stored in the memory storage unit, using the control device 28. The separating analysis itself is thus performed pressure-controlled. The corresponding operating pressure course 38 is shown in FIG. 2 by the hatched line.

During the execution of the separating analysis, the exact application of the operating pressure course 38, calculated from the reference pressure course 35, ensures that the analysis can be performed with the desired, extremely small, and essentially constant operating volume stream of the fluid 34, even without, and especially without, requiring a measurement of the work volume stream.

Between the mixing point 32 and the separating column 23, a certain dead volume is created, representing a certain delay volume. In order to take account of the contribution of this dead volume, a dead time correction is useful. This means that the time of the application of the operating pressure course is shifted back against the time of the application of the reference pressure course by a certain difference dead time, i.e. it is shifted towards later times. This difference dead time causes a certain difference delay time.

The difference dead time can be determined for example, by measuring a reference delay time in the form of a reference dead time for the fluid 34 experimentally during the application of the essentially constant reference volume stream. This can be done by using so-called dead time markers or delay time markers. The dead volume of the system can then be calculated as the product of reference dead time and the reference volume stream. An operating dead time can be calculated as the quotient of the dead volume and the chosen operating volume stream. This operating dead time corresponds to a certain operating delay time. From the operating dead time and the reference dead time, a difference dead time can be simply calculated by taking the absolute value of their difference. This difference dead time 39 corresponds to a certain difference delay time. The operating pressure course 38 can then be delayed by this difference dead time 39 with respect to the reference pressure course 35, as is shown in FIG. 2. In this manner, the additional time is taken into consideration that the fluid needs to overcome the dead volume when applying the time development of the operating pressure.

The second alternative method can be divided into two basic steps. In a first step, a reference measurement is also performed during which a time reference pressure course 40 is measured with the aid of at least one of the pressure sensors 26 which the pump 21 is used in gradient operation to deliver an essentially constant volume stream of the fluid 34 through a reference channel. This reference measurement is thus also performed volume stream controlled, using the control device 27.

Unlike in the first alternative method, the second alternative method uses a reference column 53 to perform a reference measurement. The reference flow cross-section of this reference column is much larger than the flow cross-section of the separating column 23. For reasons of simplicity, the reference column 53 is not drawn separately in FIG. 1. Instead the reference mark 53 is simply given in round brackets. In the embodiment on which the representation in FIG. 3 is based, the diameter of the reference column 53 is one millimeter whereas the diameter of the separating column 23 is only 0.1 millimeter.

In the second alternative method, the reference volume stream is also chosen relatively large to enable a sufficiently precise measurement of the volume stream, for example using one of the flow sensors 25. The resulting reference pressure course 40 over time is also suitably stored, using a memory or storage unit of the storage and computational device 29. The reference volume stream in this alternative method is set so that a laminar linear flow velocity of preferably 1 to 5 mm/s is reached in the reference column 53. This value of the flow velocity has been shown to be advantageous for the separating analysis in separating columns.

Figure 3:
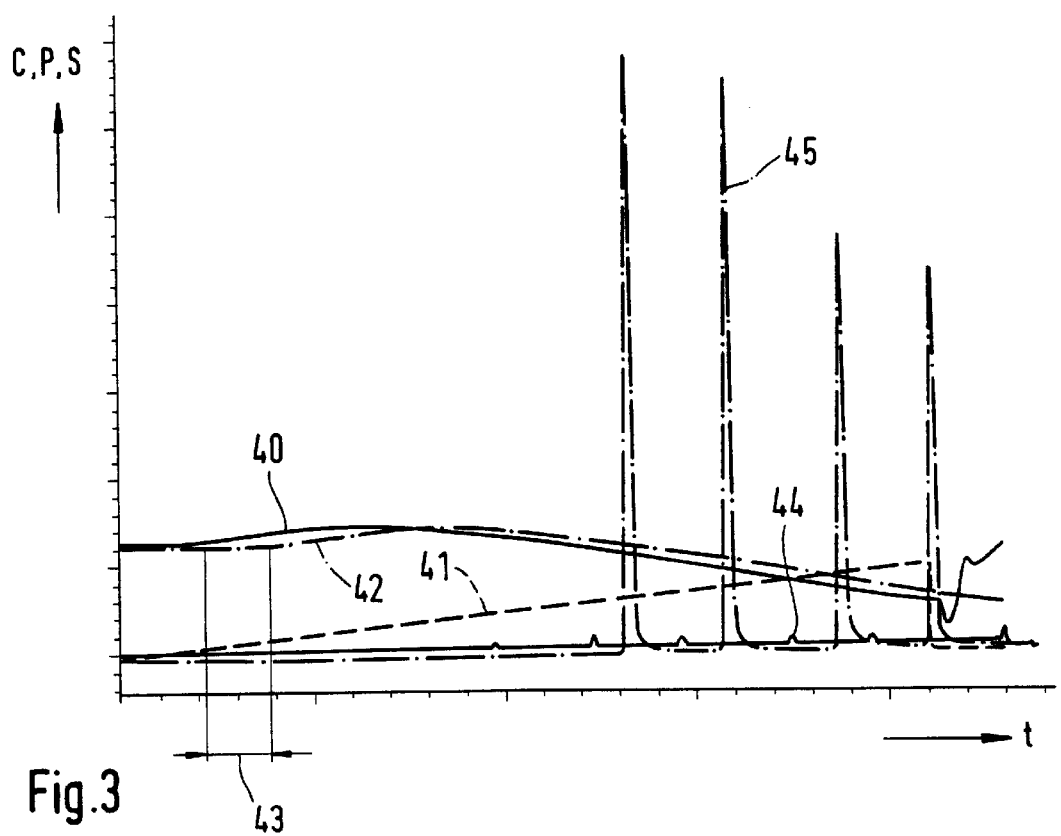
FIG. 3: a representation of two pressure profiles, a concentration profile of a fluid that is part of a fluid mixture that has time-varying flow properties, and two corresponding signal courses, each over time, that may occur when performing the method according to a second approach.

The reference pressure course 40 given as an example for such a reference measurement using a reference capillary with a diameter of 1 mm, is shown over time by the full line in FIG. 3. The reference volume stream in this case is 50 $\mu$l/min. The time parallel concentration course 41 of acetonitrile is also shown in FIG. 3 by the dashed line, wherein the concentration is again increased linearly within a certain time. The time development of the water is simply the opposite again, i.e. the concentration is decreased parallel to time.

As it is also clearly seen in FIG. 3, the volume stream controlled delivery of the fluid 34 with an essentially constant reference volume stream results in a non-linear reference pressure course 40, wherein after a certain time, an increase of pressure occurs again respectively in the range of certain concentrations of the mixture of water and acetonitrile.

In a subsequent second step, the operating measurement or the separating analysis is performed by again establishing the same time-dependent concentration course of the liquids making up the fluid 34 in the operating channel 33 and by using the control device 28 to follow the reference pressure course stored in the memory storage unit in the form of an identical operating pressure course over time. Consequently, the separating analysis itself is performed pressure-controlled in the second alternative method as well, but the time pressure courses are each identical. This alternative method uses the realization that, for identical pressures or time pressure courses the respective resulting linear flow velocities in the narrow channels or capillaries are also identical. Consequently, following the time-dependent reference pressure course during the separating analysis in the separating column also creates the same linear flow velocity of preferably 1 to 2 mm/s. By following the reference pressure course during the separating analysis, an essentially constant operating volume stream is created. In the example on which FIG. 3 is based, this operating volume stream is 50 nl/min.

FIG. 3 also clearly shows the advantage of a separating column with small flow cross-section. While by using a reference column 53 with inner diameter of 1.0 mm, the detector signals 44, recorded by the detector 24 and shown by the full line, are barely discernible, the use of a separating column 23 with an inner diameter of only 0.1 mm creates the detector signals 45 shown as the hatched line, which are clearly differentiable in height and width for the same sample amount.

When this alternative method is used for separating analyses in chromatographic separating columns, it is also advisable to perform a dead time correction because of the smaller operating volume stream and performing a time shift when applying the time-dependent pressure profile during the actual analysis, wherein the time-shift is a shift back by a difference dead time 43 corresponding to a certain difference delay time. The method for the determination of the difference dead time 43 corresponds to the method discussed above in connection with the first alternative method, so that reference will be made to the above discussion.

It is understood that due to the respective pressure-controlled execution of the separating analyses, the flow rate or volume streams should be checked and, if necessary, corrected in reasonable time intervals. A check of the volume streams is advised before every analysis. This is particularly important if several subsequent samples are to be separated automatically. This is because a residue deposit on a frit can particularly change the hydraulic resistance of a separating system, thus changing the flow rates through the operating channel. The control of the volume streams can be done manually or with the aid of sensors.

It is possible for example to perform a chromatographic procedure where the detention time of a substance between its injection and its detection is measured. Advantageous is the use of substances that are not retained by the separating column, i.e. so-called dead time markers or delay time markers. These substances are transported precisely with the current flow velocity so that their detention time is a measure for the present flow rate. Suitably, the composition of the solvent 34 in the channel 33 is kept constant.

A flow measurement can also be done indirectly. For example, the ionization stream of an ion source of a mass-selective detector can be used. It is known that the ion density depends on the flow rate. With corresponding calibration measurement with otherwise constant conditions, the ionization stream can be evaluated as an indirect measure for the volume stream.

If during the check of the volume stream it is determined that it has changed, the pressure level in pressure-controlled methods can simply be raised during the separating analysis to ensure that the desired, essentially constant volume stream is again established in the operating channel.

What is claimed is:

1. A method for the supply of volume streams of fluids in channels or capillaries with small stream cross sections, more particularly in chromatographic separation columns for analytical fluid metrology, wherein a delivery device for the delivery of a volume stream of the fluid through an operating channel and a pressure measuring device for measuring the pressure in the operating channel is provided, wherein a measurement of the volume stream is possible, said method comprising:

a) recording a reference time development of the pressure, using the pressure measuring device in the operating channel, while the delivery device delivers a reference volume stream through the operating channel of a fluid with properties, more particularly flow properties, varying over time;

b) calculation of a time development of the operating pressure which corresponds to the operating volume stream through the operating channel, which is different from the reference volume stream, using a predeterminable mathematical algorithm; and c) delivery of a fluid through an operating channel, utilizing the time development of the operating pressure determined in step b), wherein the desired work process is performed.

2. A method according to claim 1, wherein the following equation is used as the mathematical algorithm:

$$P_A = P_R \cdot k \cdot V_A / V_R$$

where $P_A$ is the operating pressure, $P_R$ is the reference pressure, k is a variable or a factor, $V_A$ is the volumetric flow rate of the operating volume stream, and $V_R$ is the volumetric flow rate of the reference volume stream.

3. A method according to claim 2, wherein said factor one is used for k.

4. A method according to claim 1, wherein said operating channels with essentially equal hydraulic resistance are used for performing said steps a) and c).

5. A method according to claim 4, wherein said chromatographic separation columns used have essentially the same length and their packing contains particles that have an essentially identical particle property.

6. A method according to claim 1, wherein a delay volume in the operating channel is taken into consideration, wherein said delay volume is formed between a mixing point where the fluid with time-varying flow properties is mixed and the separating column, and wherein the operating pressure course is corrected for a corresponding difference delay time.

7. A method according to claim 6, wherein, when the essentially constant reference volume stream is applied, a reference delay time is determined for the fluid first, from which said delay volume is derived as the product of the reference delay time and the reference volume stream and the operating delay time is calculated as the quotient of delay volume and the selected operating volume stream, and wherein these values are used to determine the difference delay time as the absolute value of the difference between the operating delay time and the reference delay time.

8. A method for the supply of volume streams of fluids in channels or capillaries with small stream cross sections, more particularly in chromatographic separation columns for analytical fluid metrology, wherein a delivery device for the delivery of a volume stream of the fluid through an operating channel and a pressure measuring device for measuring the pressure in the operating channel is provided, wherein a measurement of the volume stream is possible, said method comprising:

a) recording a reference time development of the pressure, using the pressure measuring device in a operating channel, used as a reference channel, wherein this channel has a reference stream cross section, while the delivery device delivers a reference volume stream through the operating channel of a fluid with properties, more particularly flow properties, varying over time; and b) delivery of a fluid through an operating channel, which has an operating stream cross section that is different from the reference stream cross section of the reference channel, using a time development of the operating pressure that corresponds to the time development of the reference pressure determined in step a).

9. A method according to claim 8, wherein said operating channels with essentially equal hydraulic resistance are used for performing said steps a) and b).

10. A method according to claim 9, wherein said chromatographic separation columns used have essentially the same length and their packing contains particles that have an essentially identical particle property.

11. A method according to claim 9, wherein a delay volume in the operating channel is taken into consideration, wherein said delay volume is formed between a mixing point where the fluid with time-varying flow properties is mixed and the separating column, and wherein the operating pressure course is corrected for a corresponding difference delay time.

12. A method according to claim 11, wherein, when the essentially constant reference volume stream is applied, a reference delay time is determined for the fluid first, from which said delay volume is derived as the product of the reference delay time and the reference volume stream and the operating delay time is calculated as the quotient of delay volume and the selected operating volume stream, and wherein these values are used to determine the difference delay time as the absolute value of the difference between the operating delay time and the reference delay time.

* * * * *